United States Patent [19]
Knodel

[11] Patent Number: 5,993,464
[45] Date of Patent: Nov. 30, 1999

[54] SURGICAL STAPLING INSTRUMENT

[75] Inventor: Bryan D. Knodel, Flagstaff, Ariz.

[73] Assignee: Ethicon Endo-surgery, Inc., Cincinnati, Ohio

[21] Appl. No.: 09/012,875

[22] Filed: Jan. 23, 1998

[51] Int. Cl.⁶ ................................................ A61B 17/16
[52] U.S. Cl. ........................................ 606/139; 606/167
[58] Field of Search .................................. 606/139, 153, 606/150, 151; 227/19, 180, 179

[56] References Cited

U.S. PATENT DOCUMENTS

| | | | |
|---|---|---|---|
| 3,316,914 | 5/1967 | Collito | 128/334 |
| 4,368,736 | 1/1983 | Kaster | 128/334 |
| 4,397,311 | 8/1983 | Kanshin | 128/305 |
| 4,470,415 | 9/1984 | Wozniak | 128/334 |
| 4,593,693 | 6/1986 | Schenck | 128/334 |
| 4,610,383 | 9/1986 | Rothfus et al. | 227/19 |
| 4,657,019 | 4/1987 | Walsh et al. | 128/334 |
| 4,803,984 | 2/1989 | Narayanan et al. | 128/334 |
| 4,893,622 | 1/1990 | Green et al. | 227/180 |
| 4,917,114 | 4/1990 | Green et al. | 227/179 |
| 4,930,502 | 6/1990 | Chen | 606/150 |
| 4,931,057 | 6/1990 | Cummings et al. | 606/153 |
| 4,983,176 | 1/1991 | Cushman et al. | 606/151 |
| 4,997,439 | 3/1991 | Chen | 606/216 |
| 5,089,008 | 2/1992 | Chen | 606/216 |
| 5,318,221 | 6/1994 | Green et al. | 227/178 |
| 5,356,424 | 10/1994 | Buzerak et al. | 606/223 |
| 5,413,268 | 5/1995 | Green et al. | 227/176 |
| 5,441,507 | 8/1995 | Wilk | 606/139 |
| 5,465,895 | 11/1995 | Knodel et al. | 227/176 |
| 5,501,689 | 3/1996 | Green et al. | 606/139 |
| 5,554,164 | 9/1996 | Wilson et al. | 606/167 |
| 5,676,674 | 10/1997 | Bolanos | 606/139 |
| 5,695,504 | 12/1997 | Gifford, III et al. | 606/153 |
| 5,752,644 | 5/1998 | Bolanos et al. | 277/176 |

FOREIGN PATENT DOCUMENTS

WO 97/33522   9/1997   WIPO ............................. A61B 17/32

Primary Examiner—Michael Buiz
Assistant Examiner—(Jackie) Tan-Uyen Ho
Attorney, Agent, or Firm—Dean Garner

[57] ABSTRACT

In accordance with the present invention there is provided a surgical device for joining a first and a second vessel together and creating a passageway therebetween. The device includes an implement which has proximal and distal ends and a longitudinal axis extending therebetween. The implement has a bottom member and a top member which are substantially coextensive. The top and bottom members are pivoted together at the proximal end so that a wall of each of the first and second vessels can be held between the top and bottom portions. The device includes a mechanism for joining the first and second vessels together along two joining lines which are substantially parallel to each other and to the longitudinal axis of the implement. The lines have distal and proximal ends. The device further includes a blade for severing the first and second vessels between the joining lines so as to create a passageway through the vessels. The blade operates such that it is able to cut the vessels along a cut line which has a proximal end that is distal to the proximal ends of the joining lines, and a distal end that is proximal to the distal ends of the joining lines.

5 Claims, 16 Drawing Sheets

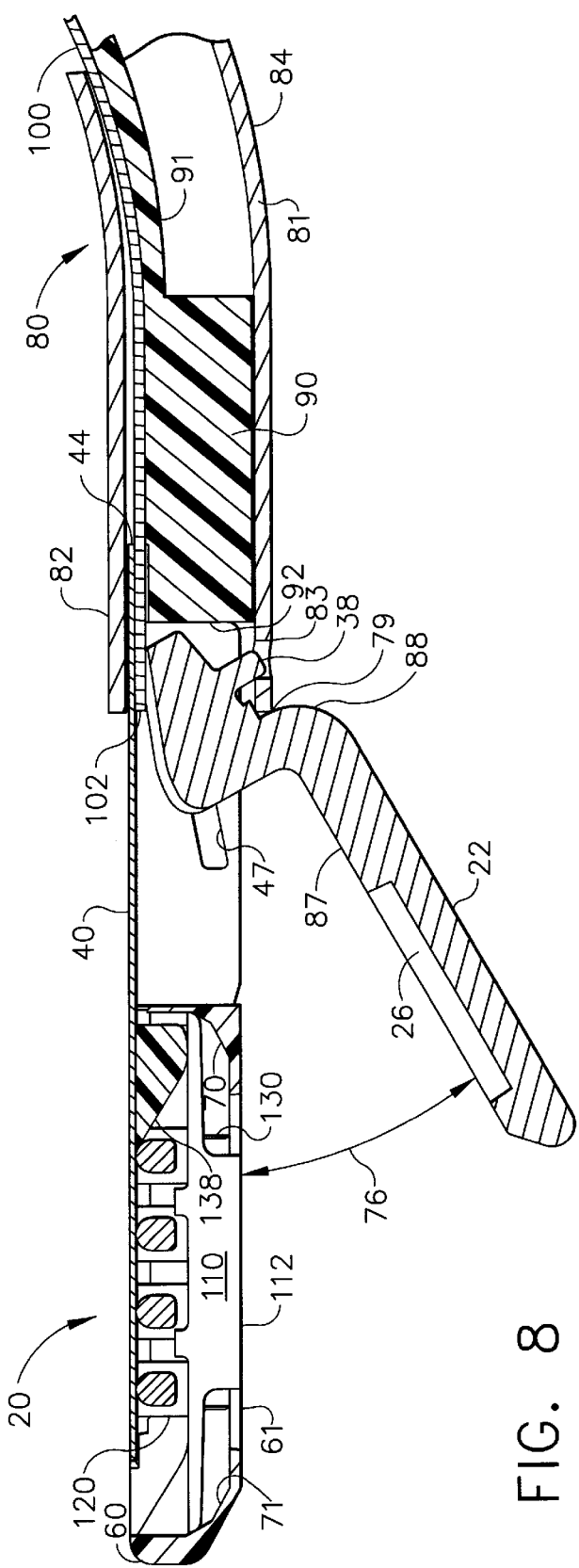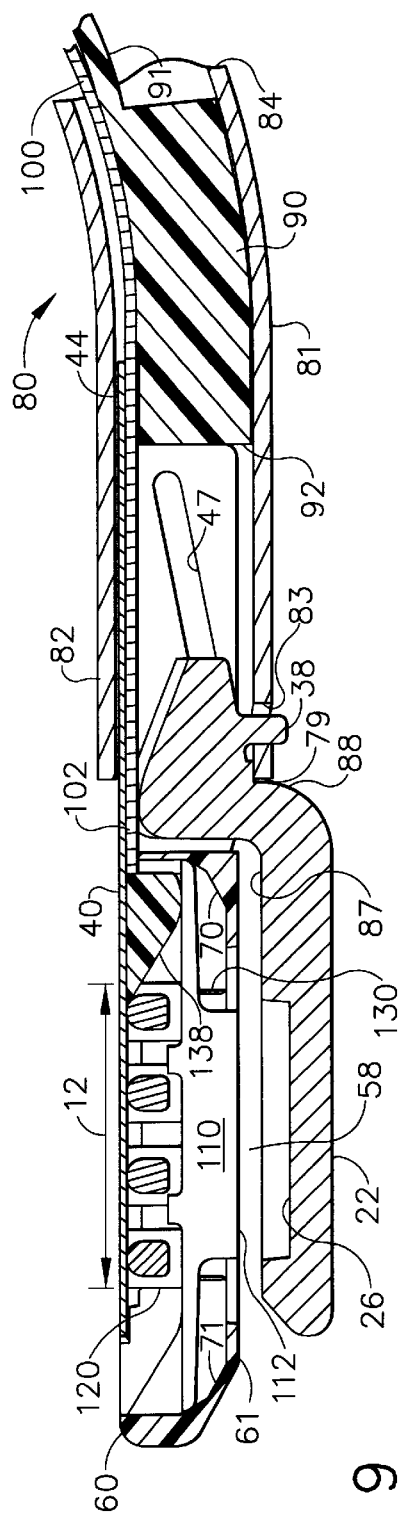
FIG. 8
FIG. 9

SURGICAL STAPLING INSTRUMENT

FIELD OF THE INVENTION

The present invention relates to devices and methods for surgically performing anastomosis of hollow organs or vessels. More particularly, it relates to vascular anastomosis devices for joining the end of a graft vessel, such as a coronary bypass graft, to the side wall of a target vessel, such as the aorta or a coronary artery.

BACKGROUND OF THE INVENTION

Creating an anastomosis, or the surgical formation of a passage between two normally distinct vessels, is a critical step of many surgical procedures. This is particularly true for coronary artery bypass graft (CABG) procedures in which one or more graft vessels are joined to the coronary arteries distal to the diseased portion in order to improve the blood supply to the myocardium (heart muscle). The graft vessels typically used are the saphenous vein of the leg or the radial artery of the arm. Also, the internal mammary (IMA) artery is commonly rerouted from its original position and attached to the lower anterior descending coronary artery (LAD) to restore blood flow to the left ventricle of the heart. When using harvested vessels, an anastomosis must be performed on both the proximal and distal ends of the graft vessel. For the case using the IMA, the anastomosis is made only at the distal end, or pedicle, of the IMA.

Currently the method of hand suturing the vascular anastomosis during a CABG is preferred by surgeons. The suturing method, however, is very time consuming, requiring several minutes per anastomosis even for an experienced surgeon. In some cases the blood flow in the newly joined vessels may be poor or there may be leaks, and the surgeon must remove the stitches and repeat the suturing procedure. In surgical procedures involving multiple bypass grafts, the time accumulated for doing the suturing is very substantial, putting the patient at risk and increasing the cost of the surgical procedure. Hand suturing also requires a high level of skill and is not easily mastered by many surgeons. It is especially difficult to suture if the anastomosis site is not easily accessed or viewed.

In the CABG procedure, access to the heart is obtained via a median sternotomy in which the rib cage is split longitudinally on the midline of the chest, and the left and right rib cages are spread apart. This method allows very good access to the heart but is very traumatic to the patient, and a lengthy recovery time (1–2 weeks) in the hospital is required. More recently, a cardiac procedure known as MIDCAB (Minimally Invasive Direct Coronary Artery Bypass) using a small, left thoracotomy (incision between the ribs on the left chest) directly above the heart has become more widely used to reduce the patient's pain and recovery time. In this procedure, however, the surgical access to the heart and visibility of it are significantly reduced, and hand suturing may be more difficult than when using a median sternotomy.

A number of devices for augmentation of the suturing techniques for vascular anastomosis have been developed. These devices attempt, with varying degrees of success, to reduce the difficulty in repeatedly passing a needle and thread through the blood vessel walls. Recent examples are found in U.S. Pat. No. 5,571,090 issued to Sherts on Nov. 5, 1996, U.S. Pat. No. 4,803,984 issued to Narayanan on Feb. 14, 1989, and U.S. Pat. No. 5,545,148 issued to Wurster on Aug. 13, 1996. In Sherts and Narayanan, the individual stitches must still be made one at a time and, therefore, the procedure is still time consuming. In addition, the working ends of the Wurster and Sherts devices appear to obstruct the view of the needle tip, and so precise placement of the stitch might be difficult in some situations.

Devices incorporating rings or fittings have been tried for end-to-side anastomosis. Examples are U.S. Pat. No. 4,366,819 issued to Kaster on Jan. 4, 1983 and U.S. Pat. No. 4,657,019 issued to Walsh, et al, on Apr. 14, 1987. These devices have several disadvantages and, therefore, have not become widely used by surgeons. The devices incorporate small, separate parts which must be manipulated into the blood vessels using special tools and techniques. The steps for assembly of such devices to the blood vessels may become more difficult as less surgically invasive procedures are used. In addition, the necessary manipulation of the vessels traumatize the delicate vessel walls, thus jeopardizing the ability of the vessels to heal properly. The presence of a portion of a ring or fitting in the blood stream may also inhibit the formation of a smooth, endothelial lining on the inner wall of the vessels.

Surgical staplers have been widely used by surgeons for many surgical procedures. Circular staplers and linear stapling and cutting instruments are well known in the art for the anastomosis of bowel tissue, but have not yet been made available to surgeons in miniature versions suitable for vascular anastomosis. Circular staplers are used primarily for end-to-end anastomosis of bowel tissue. For coronary procedures, the end-to-end type of anastomosis is not preferred because it requires the coronary artery to be completely severed from its original blood supply to be joined to the graft vessel. This could only be used in relatively infrequent cases when the coronary artery is completely occluded proximal to the location for the anastomosis. Circular staplers also have been used for the end-to-side type of anastomosis on large organs such as bowel. A key disadvantage of a circular stapler for this application is that one hollow organ must be joined to the side of the other hollow organ at about a 90 degree angle. In vascular anastomosis, it is often desirable to join the graft vessel to the target vessel at an acute angle to facilitate laminar blood flow through the joined vessels, or to avoid kinking of the graft vessel. Also, the size of the passageway between the joined vessels is limited by the diameter of the graft vessel. For a side-to-side anastomosis, the passageway size can be made to very large relative to the vessel diameters by choosing the appropriate length of staple joining lines.

In the PCT application WO 97/16122 filed by Rygaard on Oct. 31, 1995, an instrument and method is shown for using a miniature, circular stapler in an end-to-side anastomosis of blood vessels. However, this device still requires substantial manipulation of the vessels as the device is assembled together and operated. This is often difficult to do with very limited access to the surgical site, and also could lead to the inability of the vessels to heal together properly. In addition, visualization of the vessels at the anastomosis while using this device is significantly obstructed by the distal end of the device.

Linear stapling and cutting instruments, usually referred to as linear cutters (see, for example, U.S. Pat. No. 5,465,895, issued to Knodel, et al, on Nov. 14, 1995 and which is hereby incorporated herein by reference) are primarily used to hemostatically transect tissues to be removed from the body, but may also be used to anastomose organs side-to-side. Such devices have proven to be time-saving, reliable, and relatively easy to use by surgeons. The current stapling devices, however, are not designed to be made into miniaturized versions that would allow them to be useful for vascular anastomosis, and, as is discussed below, there are difficulties in making miniaturized versions.

A linear cutter has two forks forming an implement on the distal end of the instrument. One fork is a metal channel adapted to receive a staple cartridge. The cartridge contains numerous surgical staples aligned longitudinally into a number (usually four or six) of rows. The other fork is a metallic anvil containing an equal number of pockets, one for each staple. When tissue is clamped between the two forks, a drive member actuated on the handle, pushes a number of wedges (usually 2) in the distal direction. The wedges bear against cam surfaces on a number of drivers within the staple cartridge, causing the drivers to push the staples out of the cartridge, through the tissue, and into the staple pockets on the anvil. As each staple is completely emitted from the cartridge, the staple forms in the anvil staple pocket, thus clinching the tissue held therebetween. As a drive member pushes the wedge in the distal direction, it also pushes a knife which is slightly proximal to the wedge. The knife cuts through all the tissue held in the forks except for at the distal most end where it stops at a location just proximal to the end of the staple lines. Then the wedges and knife are returned to their starting location either manually or by a spring return mechanism within the handle of the instrument.

When using a conventional linear cutter for creating a side-to-side anastomosis of large organs, the severed end of a first hollow organ (such as a portion of the small intestine) is placed over the anvil. Next the severed end of a second hollow organ (such as another portion of the small intestine) is placed over the staple cartridge channel. The tissue is clamped together, stapled and cut. This must then be followed by a second application of the device perpendicular to the first application in order to close the open ends of the two joined organs. The result is a passage between the two joined organs. In time, the tissues grow together, given an adequate blood supply. As the joined organs heal together, the passage between the organs straightens. More detailed descriptions along with illustrations showing the use of linear cutting staplers for side-to-side anastomosis of bowel, as well as other procedures, can be found in the *Atlas of Abdominal Surgery*, Braasch, et al, Chapter 10, published by W. B. Saunders Co., 1991.

Prior art linear cutters, however, are not practical for use on small blood vessels. In addition to the problems of attempting to manufacture components based on designs simply scaled down from the prior art linear cutters, there would be other difficulties with using prior art linear cutters for small vessel anastomosis. When a conventional linear cutter is used on tissue, the knife cuts through all the tissue clamped between the forks up to a location just proximal to the distal end of the staple line, severing the joined organs at their open ends where the forks are inserted. Therefore, instead of creating a closed loop passageway between the sides of the organs, an open, V-shaped passageway is created. This could cause a number of difficulties and problems when creating anastomosis in very delicate vessels such as the coronary artery.

Regardless of the above, linear cutters are simple, effective and easy to use surgical devices. Therefore there has been a desire for a linear cutter which can provide anastomosis of very small hollow organs such as blood vessels, but which overcomes the above mentioned problems. Such a device should allow the creation of a passage between the vessels in one step, after preparation of the vessels, and that the passage have an unbroken, flexible circumference. It is further desirable that the device require minimal manipulation of the blood vessels. It is also desirable to provide a device which creates the anastomosis without exposing blood flow to a significant amount of foreign material and allows rapid healing of the endothelial lining inside the blood vessels. Further, it is desirable to have such a device which is adapted to be used in traditional open cardiac procedures (CABG), minimally invasive procedures such as MIDCAB, and also adaptable to endoscopic procedures. The present invention provides such a device.

SUMMARY OF THE INVENTION

In accordance with the present invention there is provided a surgical device for joining a first and a second vessel together and creating a passageway therebetween. The device includes an implement which has proximal and distal ends and a longitudinal axis extending therebetween. The implement has a bottom member and a top member which are substantially coextensive the top and bottom members are pivoted together at the proximal end so that a wall of each of the first and second vessels can be held between the top and bottom portions. The device includes a mechanism for joining the first and second vessels together along two joining lines which are substantially parallel to each other and to the longitudinal axis of the implement. The lines have distal and proximal ends. The device further includes a blade for severing the first and second vessels between the joining lines so as to create a passageway through the vessels. The blade operates such that it is able to cut the vessels along a cut line which has a proximal end that is distal to the proximal ends of the joining lines, and a distal end that is proximal to the distal ends of the joining lines.

BRIEF DESCRIPTION OF THE DRAWINGS

The novel features of the invention are set forth with particularity in the appended claims. The invention itself, however, both as to organization and methods of operation, together with further objects and advantages thereof, may best be understood by reference to the following description, taken in conjunction with the accompanying drawings in which:

FIG. 8 is a side elevational view in section of the implement of the surgical device in a second position, corresponding with FIG. 6.

FIG. 9 is a side elevational view in section of the implement of the surgical device with the anvil in a closed position, corresponding with FIG. 7.

DETAILED DESCRIPTION OF THE PREFERRED EMBODIMENT OF THE INVENTION

Figure 1:
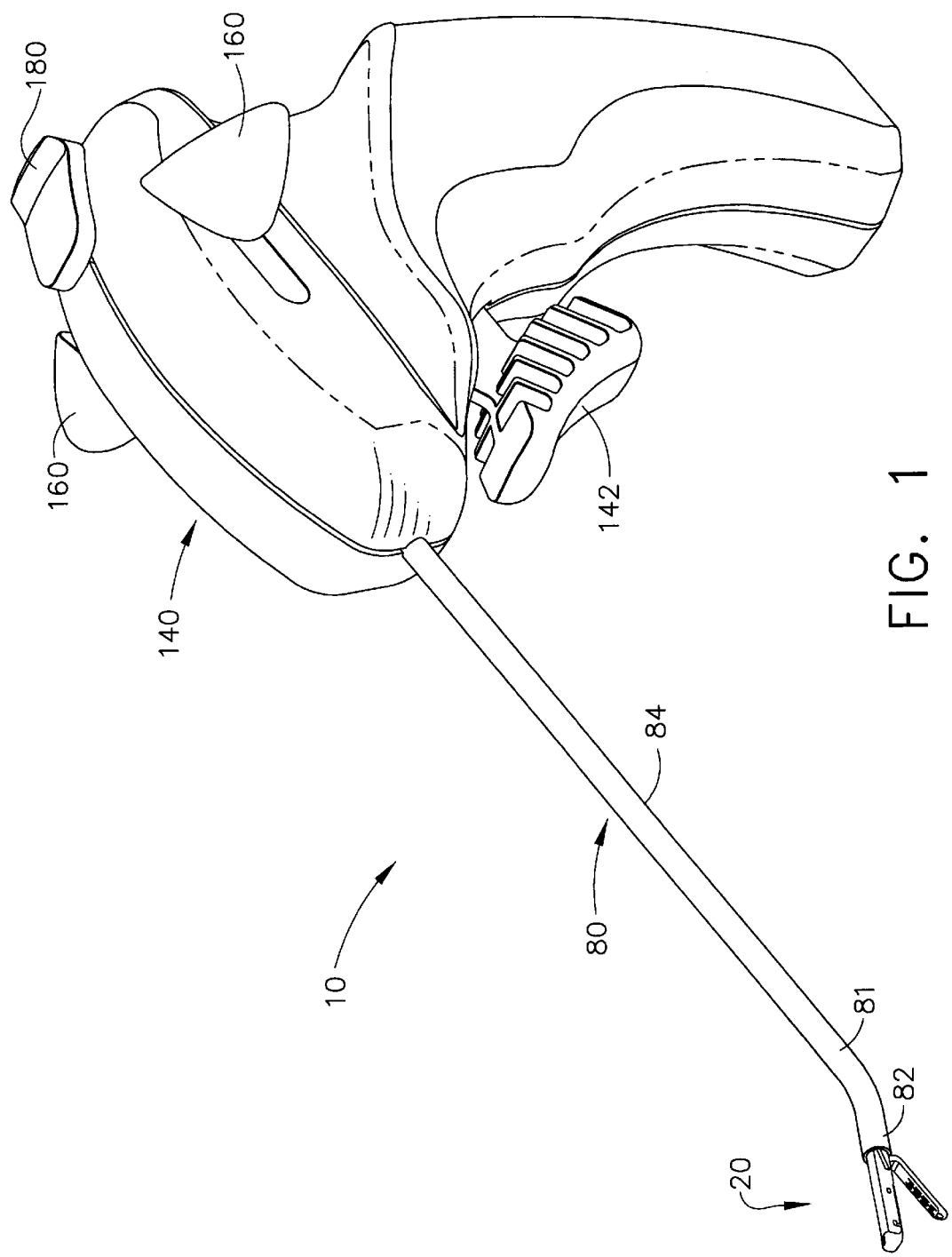
FIG. 1 is an isometric view of the surgical device constructed in accordance with a preferred embodiment of this invention.

Referring now to the drawings in detail wherein like numerals indicate the same elements throughout the views, there is shown in FIG. 1 is an isometric view of the preferred embodiment of the present invention which is a surgical device 10. Device 10 includes a handle 140, a shaft 80, and an implement 20. The handle 140 has a pistol grip and includes a closing trigger 142, an actuator 160, and a release button 180. The ergonomic shape of the handle 140 and placement of the closing trigger 142, actuator 160, and release button 180 allow the one-handed use of the surgical device 10. Other ergonomic shapes of the handle 140 and other shapes/placements of the associated components are possible without limiting the scope or intent of the present invention. The shaft 80 has a distal end 82, a proximal end 86 (see FIG. 5) inside the handle 140, and a bend 81 near the distal end 82. Bend 81 is provided to facilitate the placement of the implement at the surgical site, such as at the coronary artery on the surface of the heart. The visible portion of shaft 80 is a tube 84, preferably made from round, stainless steel tubing. The shaft provides a means of access of the implement 20 to the surgical site and contains the means for transferring the surgeon's hand forces imparted to the handle 140 to the implement 20. The surgical device 10 can be used by the surgeon in a surgical procedure to join together two hollow organs, preferably with either a side-to-side, or a functional end-to-side anastomosis using surgical wire staples. In the following description, the surgical device 10 will be described in use with blood vessels, although it can be used for other hollow organs, and it can also be used for the hemostatic transection of other bodily tissues.

Figure 2:
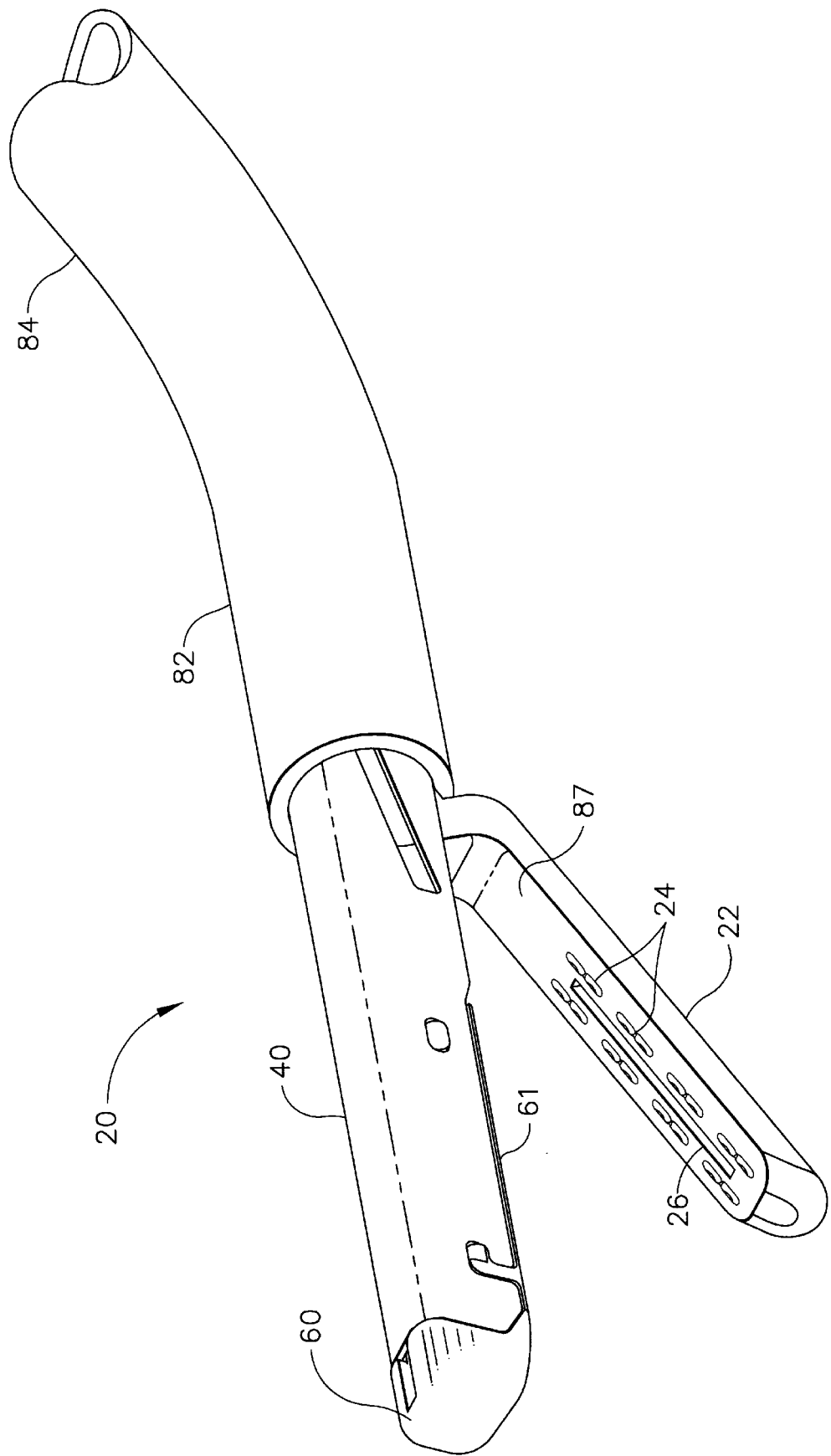
FIG. 2 is an isometric view illustrating details of the implement of the surgical device.

FIG. 2 is an enlarged, isometric view of the implement 20 and the distal end 82 of the tube 84. The implement 20 includes a channel 40 retained slidably in the distal end 82 of tube 84. Channel 40 is adapted to receive a cartridge 60 which has a clamping surface 61. The implement 20 also includes an anvil 22 which has a plurality of staple pockets 24 aligned into two longitudinal rows on clamping surface 87. Anvil 22 includes a knife slot 26. The anvil 22 is pivotably attached to channel 40 and retained in the distal end 82 of tube 84. The anvil 22, channel 40, and cartridge 60 function in cooperation to clamp onto bodily tissues contained between clamping surfaces 87 and 61.

Figure 3:
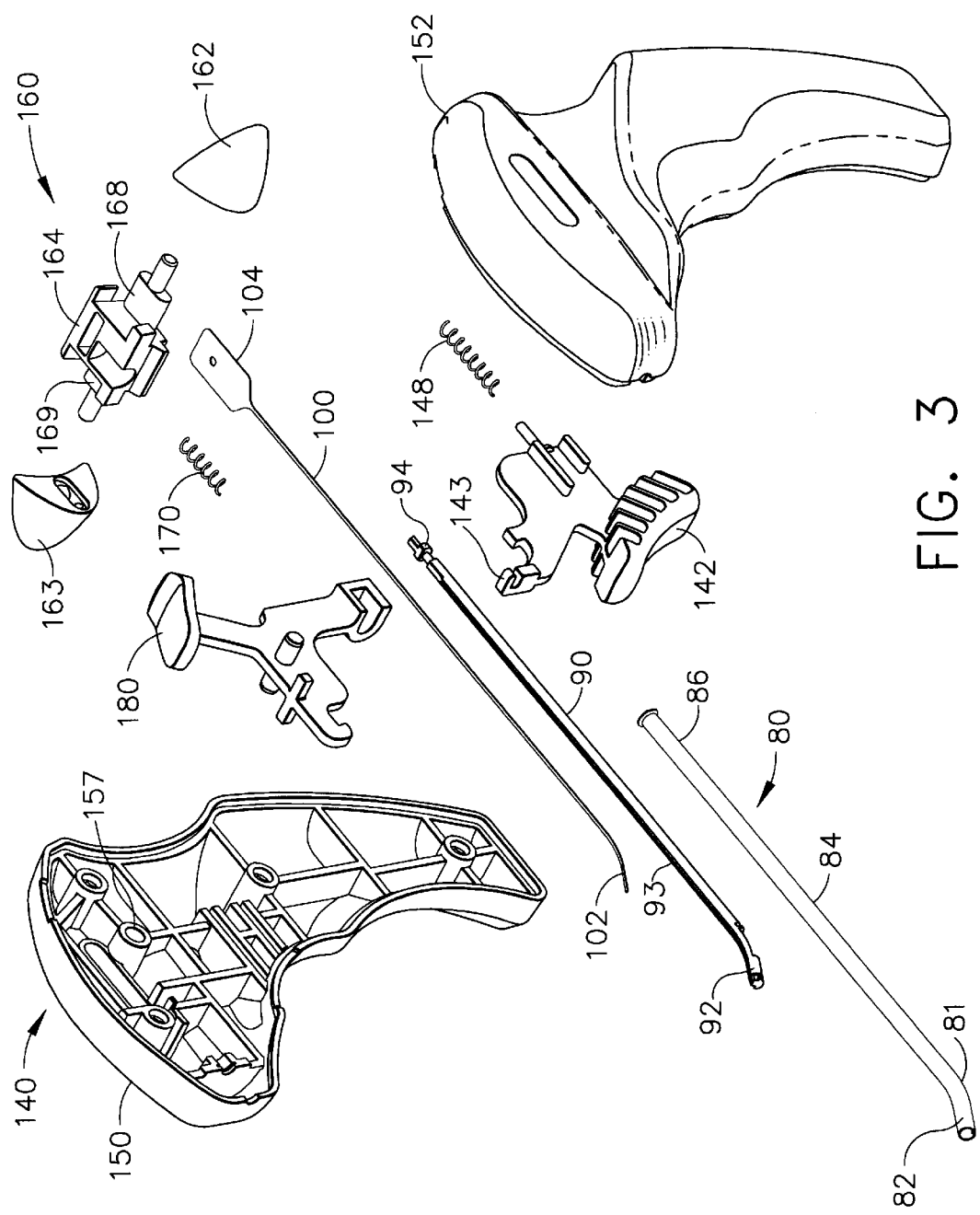
FIG. 3 is an exploded isometric view of the handle for the surgical device.

Turning now to FIG. 3, the components of the handle 140 and shaft 80 are shown in an exploded isometric view. The handle 140 includes a right cover 150 and a left cover 152, each made from a rigid, medical grade plastic, and together which support the closing trigger 142, the actuator 160, and the release button 180. Shown in right cover 150 is a right release button pivot 157 in which release button 180 pivots. The actuator 160 includes a left and right button, 162 and 163 respectively, and a slide 164 having left and right slide tabs, 168 and 169 respectively. The buttons 162 and 163, and the slide 164 are made from a rigid, medical grade plastic, as are the closing trigger 142 and the release button 180. The handle 140 further includes an actuator spring 170 and a closing trigger spring 148, each made from a spring steel wire. The shaft 80 includes, disposed within tube 84, a drive member 100 which is made preferably from a stainless steel and has a flattened, proximal end 104 for attachment to slide 164. Drive member 100 moves longitudinally within a track 93 along the length of a closing member 90 which has a proximal end 94 and a distal end 92, and is made from a medical grade plastic with some amount of flexibility. The drive member 100 moves distally from a first position to a second position to actuate the work portion of the implement 20 (see FIG. 2). Proximal end 94 of closing member 90 attaches to rod retaining end 143 of closing trigger 142.

Figure 4:
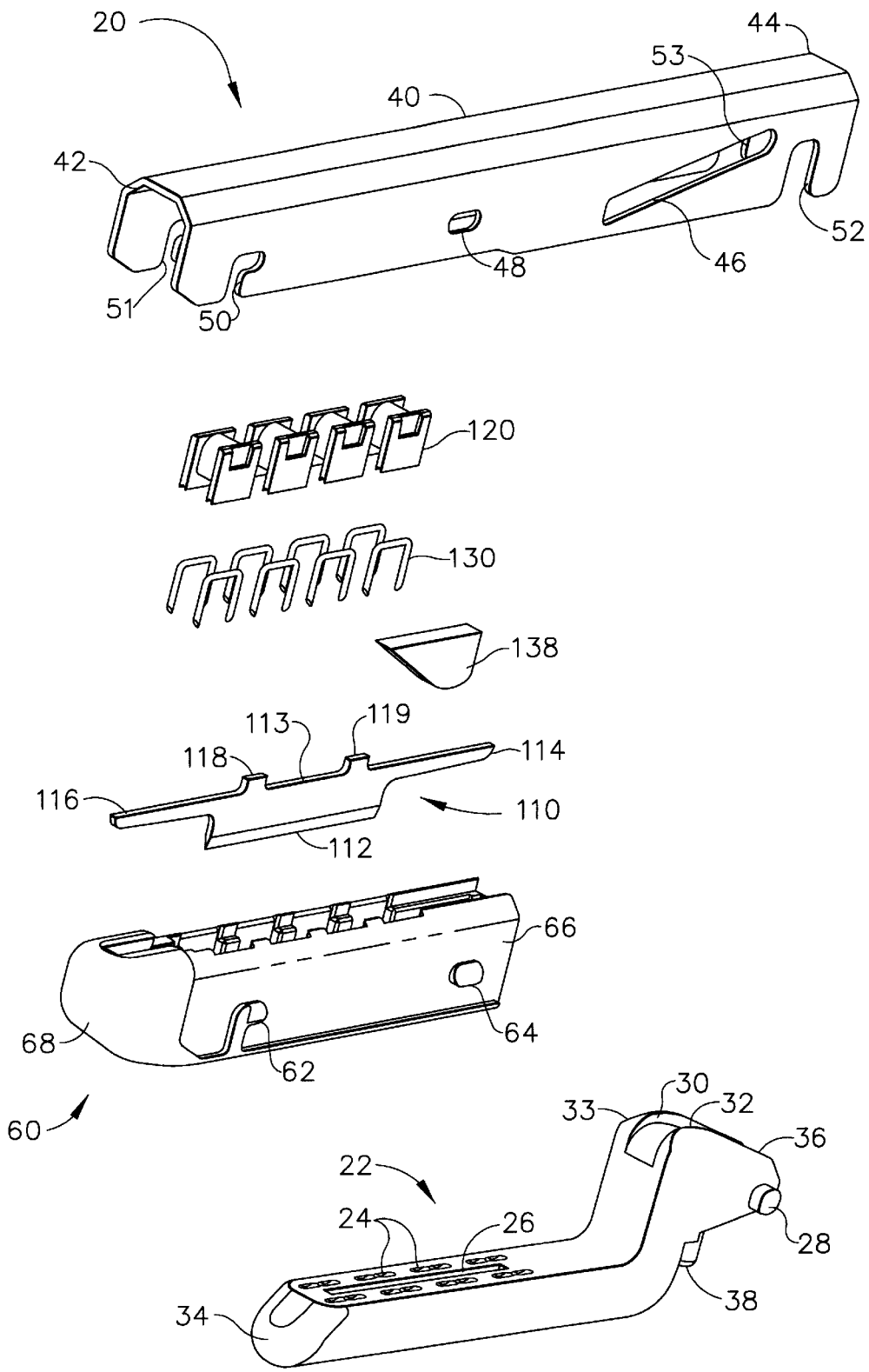
FIG. 4 is an exploded isometric view illustrating the details of the components that comprise the implement of the surgical device.

Now looking at FIG. 4, an exploded isometric view of the implement 20 is shown, revealing the work portion of the present invention. This portion includes eight, surgical steel wire staples 130, four staple drivers 120 which are made from a rigid, medical grade plastic, a wedge 138 made from a metal or a rigid, medical grade plastic, and a knife 110 made from a medical grade, metal alloy exhibiting highly elastic properties. In this embodiment, the metal alloy is preferably a nickel-titanium alloy. Knife 110 includes an integral, proximal spring end 114 and integral, distal spring end 116, a cutting edge 112, a first tab 118, a second tab 119, and a blunt edge 113. The cartridge 60 has a distal end 68 and a proximal end 66 and is made from a rigid, medical grade plastic. The cartridge 60 is adapted to receive the drivers 120, the staples 130, the wedge 138, and the knife 110. The cartridge has a left detent tab 64 and right detent tab 65 (see FIG. 30) to locate into a left detent hole 48 and a right detent hole 49 (not shown) of the channel 40. Cartridge 60 also has a left alignment projection 62 and a right alignment projection 63 (see FIG. 30) to snap tightly into a left L-slot 50 and a right L-slot 51 respectively. In this embodiment, the cartridge 60 is not intended to be removed from the channel 40 during the surgical procedure using the surgical device 10. However, those skilled in the art can appreciate that this cartridge 60 could be modified to be reloadable into the channel 40, in a way much like is done currently with commercially available linear, cutting, surgical staplers.

Figure 17:
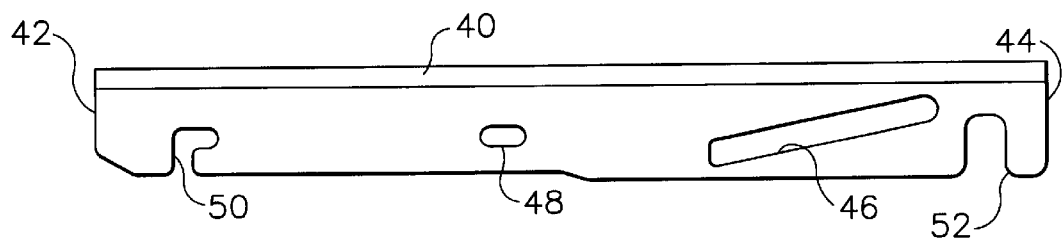
FIG. 17 is a side elevational view of the channel of the implement of FIG. 4.

Skipping briefly to FIGS. 17–29, in FIG. 17 a side view of the channel 40 is shown separately for clarity.

Figure 18:
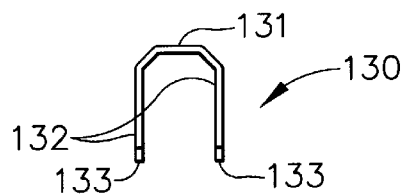
FIG. 18 is a front elevational view of the channel of FIG. 17.

FIG. 18 is a side view of the staple 130 which comprises a crown 131, two legs 132, and two staple points 133. The width of the crown 131 and the length of the legs 132 are each 1.016 mm (0.040 inches). The staple wire diameter is 0.114 mm (0.0045 inches). These staple dimensions may vary without changing the scope or intention of the present invention.

Figure 19:
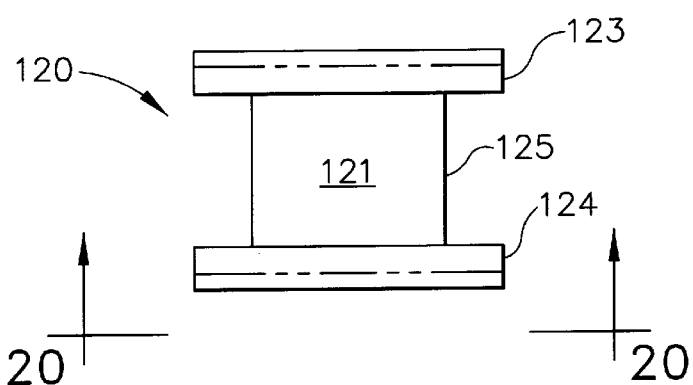
FIG. 19 is a plan view of the driver of the cartridge of FIG. 4.
Figure 20:
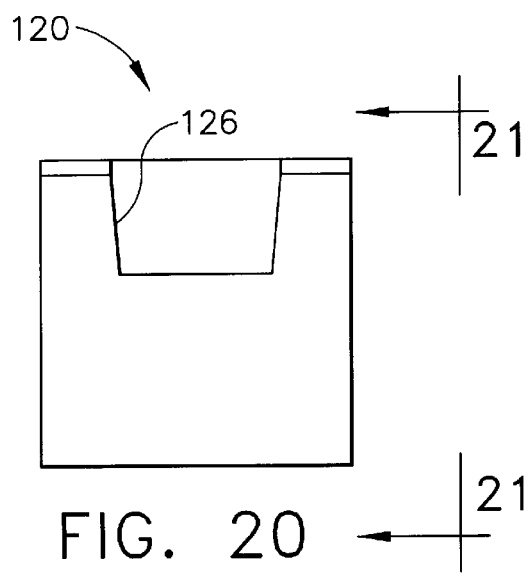
FIG. 20 is a side elevational view of the driver of FIG. 19 taken along line 20—20.
Figure 21:
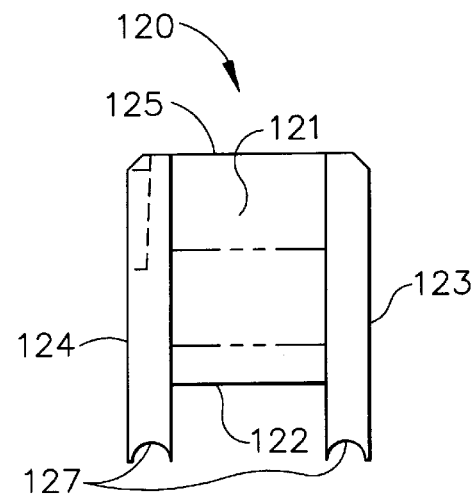
FIG. 21 is a front elevational view of the driver in FIG. 19 taken along line 21—21 of FIG. 20.

FIGS. 19, 20, and 21 are alternative views of one of the drivers 120. In the top view of FIG. 19, a first wing 123 is joined to a second wing 124 by a bridge 125. Bridge 125 includes a cam surface 121. FIG. 20 is a view as indicated by line 20—20 in FIG. 19, and shows a recess 126 which is provided for the location of the plastic injection molding gate. FIG. 21 is a view as indicated by line 21—21 in FIG. 20 and reveals the staple driving surfaces 127 and the bottom surface 122.

Figure 22:
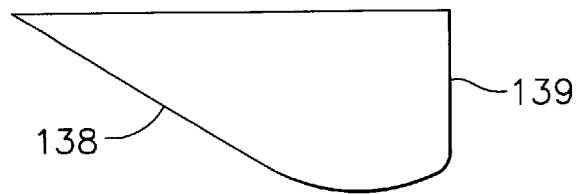
FIG. 22 is a side elevational view of the wedge of the cartridge of FIG. 4.
Figure 23:
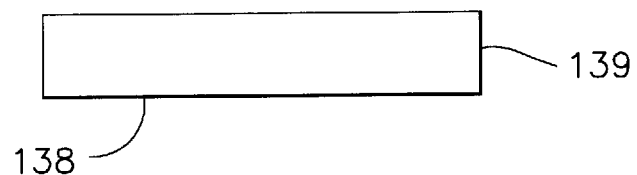
FIG. 23 is a plan view of the wedge of FIG. 22.

FIGS. 22 and 23 are alternative views of the wedge 138, including blunt edge 139, shown separately for clarity.

Figure 24:
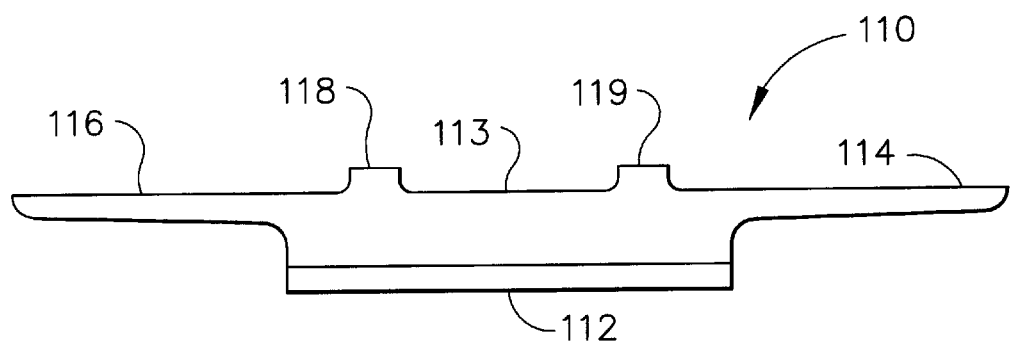
FIG. 24 is a side elevational view of the knife of the implement of FIG. 4.
Figure 25:
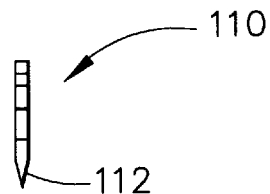
FIG. 25 is a front elevational view of the knife of FIG. 24.

FIGS. 24 and 25 are alternative views of the knife 110, shown separately for clarity.

Figure 26:
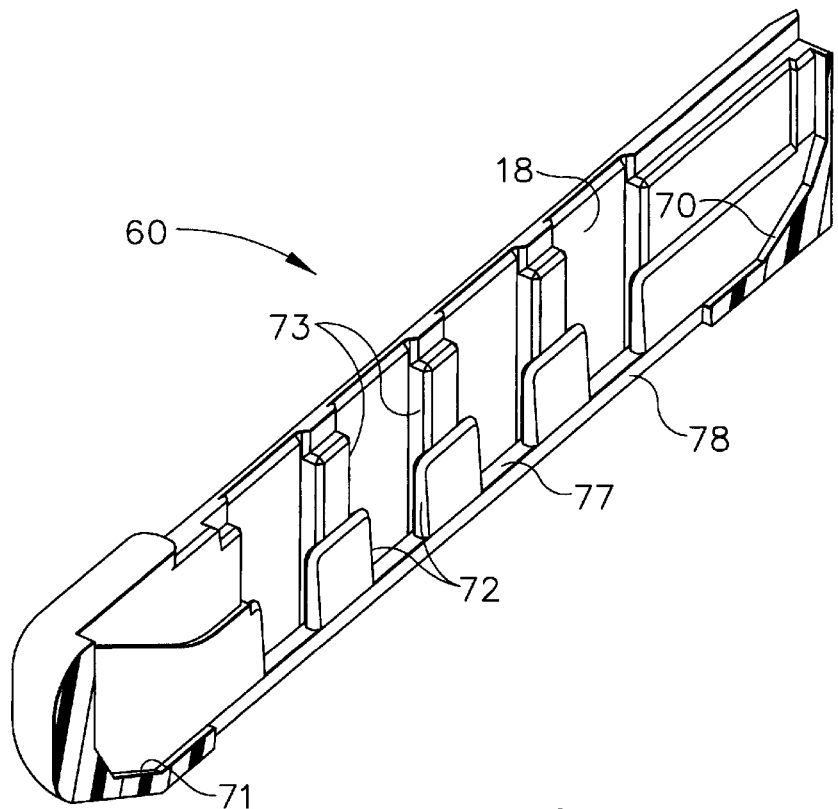
FIG. 26 is an isometric sectional view of the cartridge of FIG. 4.
Figure 27:
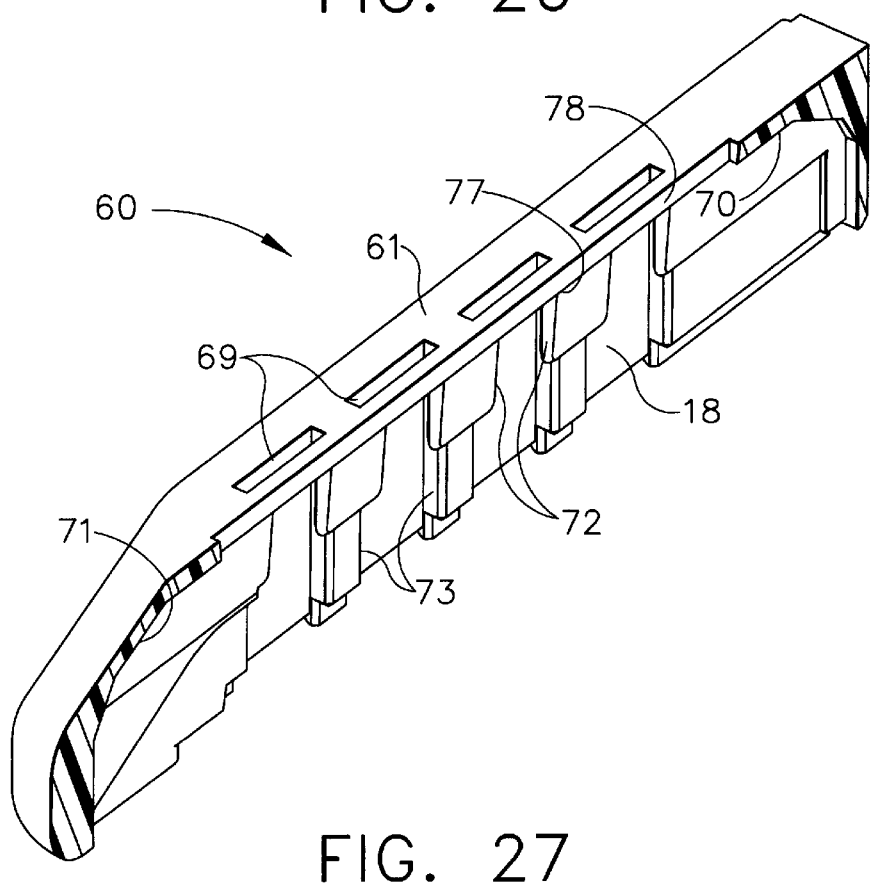
FIG. 27 is an inverted isometric sectional view of the cartridge of FIG. 26.

FIGS. 26 and 27 are isometric sectional views of the cartridge 60, revealing the internal features, including a plurality of columns 73, a plurality of fingers 72, a proximal ledge 70, a distal ledge 71, a plurality of driver spaces 18, a knife slot 78, and a driver ledge 77. Also shown is clamping surface 61 and staple holes 69.

Figure 28:
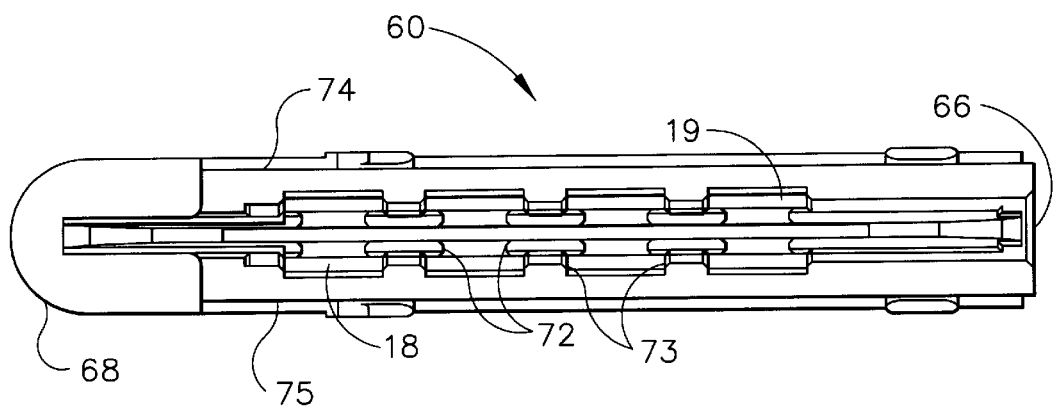
FIG. 28 is a plan view of the cartridge of the distal end assembly of FIG. 4.
Figure 29:
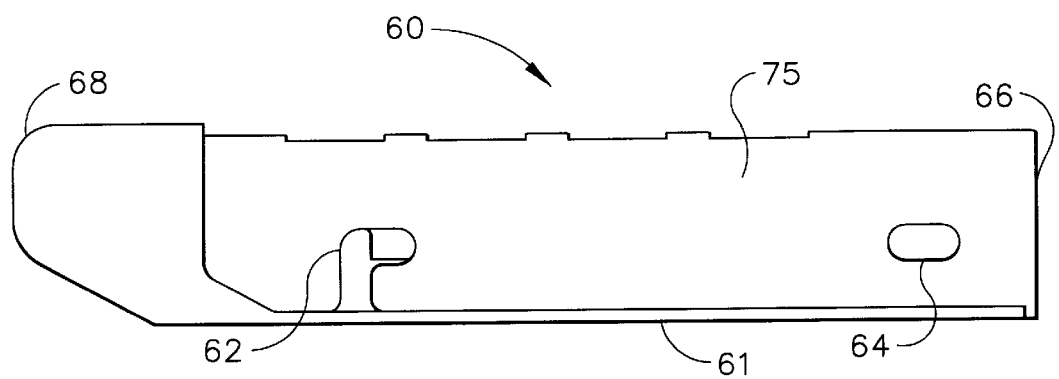
FIG. 29 is a side elevational view of the cartridge of FIG. 28.
Figure 30:
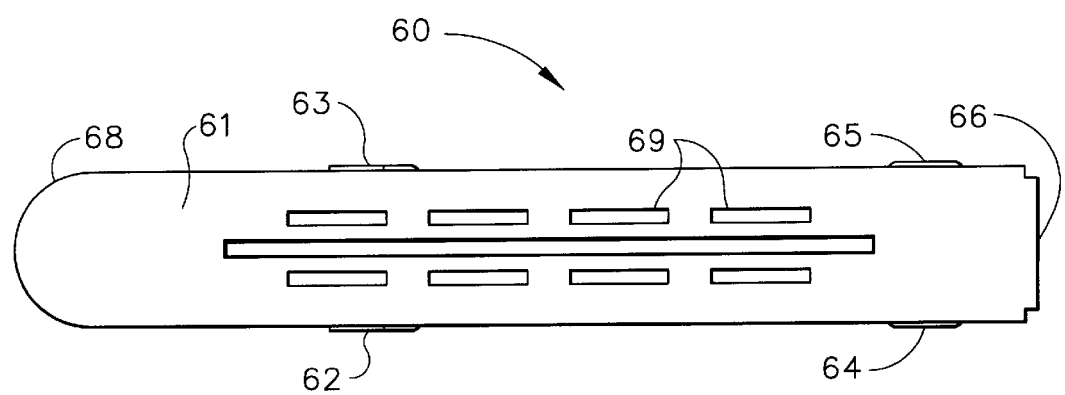
FIG. 30 is a bottom view of the cartridge of FIG. 28.

FIGS. 28, 29, and 30 are alternative views of the cartridge 60, shown separately for clarity. FIGS. 28 and 29 show recessed surfaces 74 and 75 which assemble closely against the insides of channel 40 (see FIG. 4). Referring to FIG. 28, the right driving spaces 18 and the left driving spaces 19 contain the staples 130 (see FIG. 17). The staple points 133 (FIG. 17) are directed towards the clamping surface 61 of the cartridge 60 (see FIG. 29) and slightly recessed below the clamping surface 61. The first and second wings, 123 and 124, of driver 120 shown in FIG. 19 fit slidably into driving spaces 18 and 19 shown in FIG. 28, so that staple crowns 131 contact and are driven by driving surfaces 127 of the drivers 120. The movement of each driver 120 in the driving direction perpendicular to the clamping surface 61 is substantially guided by the sliding contact on finger 72 with the bridge 125 of the driver 120.

Figure 31:
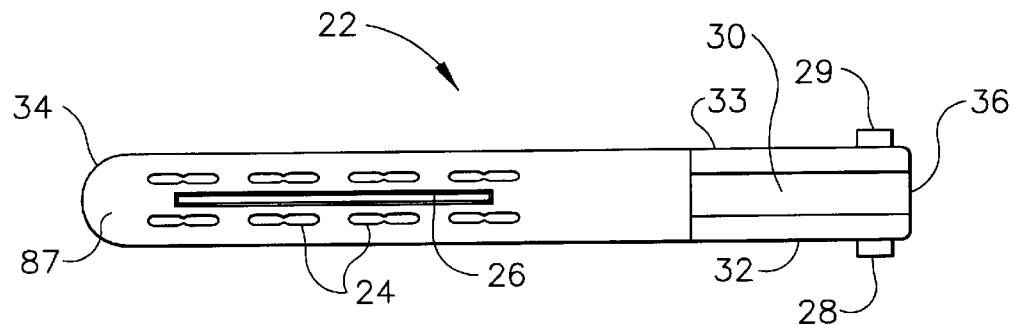
FIG. 31 is a plan view of the anvil of FIG. 4.
Figure 32:
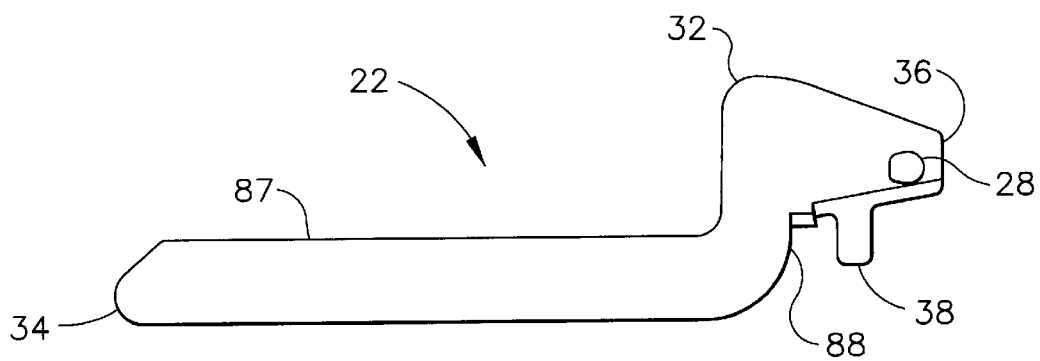
FIG. 32 is a side elevational view of the anvil of FIG. 31.
Figure 33:
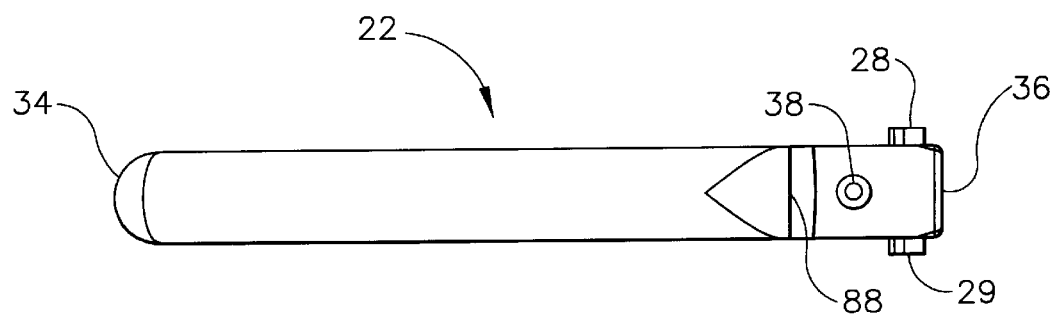
FIG. 33 is a bottom view of the anvil of FIG. 31.

Returning now to FIG. 4, the proximal end 36 of the anvil 22 has a left guiding post 28 and a right guiding post (not shown) which fit slidably and pivotably into a left anvil slot 46 and a right anvil slot (not shown) respectively. A pulling tab 38 is provided for the opening of the anvil and is located between and slightly distal to the right and left guiding posts on the proximal end 36. Also on proximal end 36 of anvil 22 is an opening 30 between left pivot heel 32 and right pivot heel 33. Opening 30 provides additional clearance for distal end 102 of drive member 100 (see FIG. 3) to pass through freely. FIGS. 31, 32, and 33 are alternative views of the anvil 22, shown separately for clarity.

Figure 5:
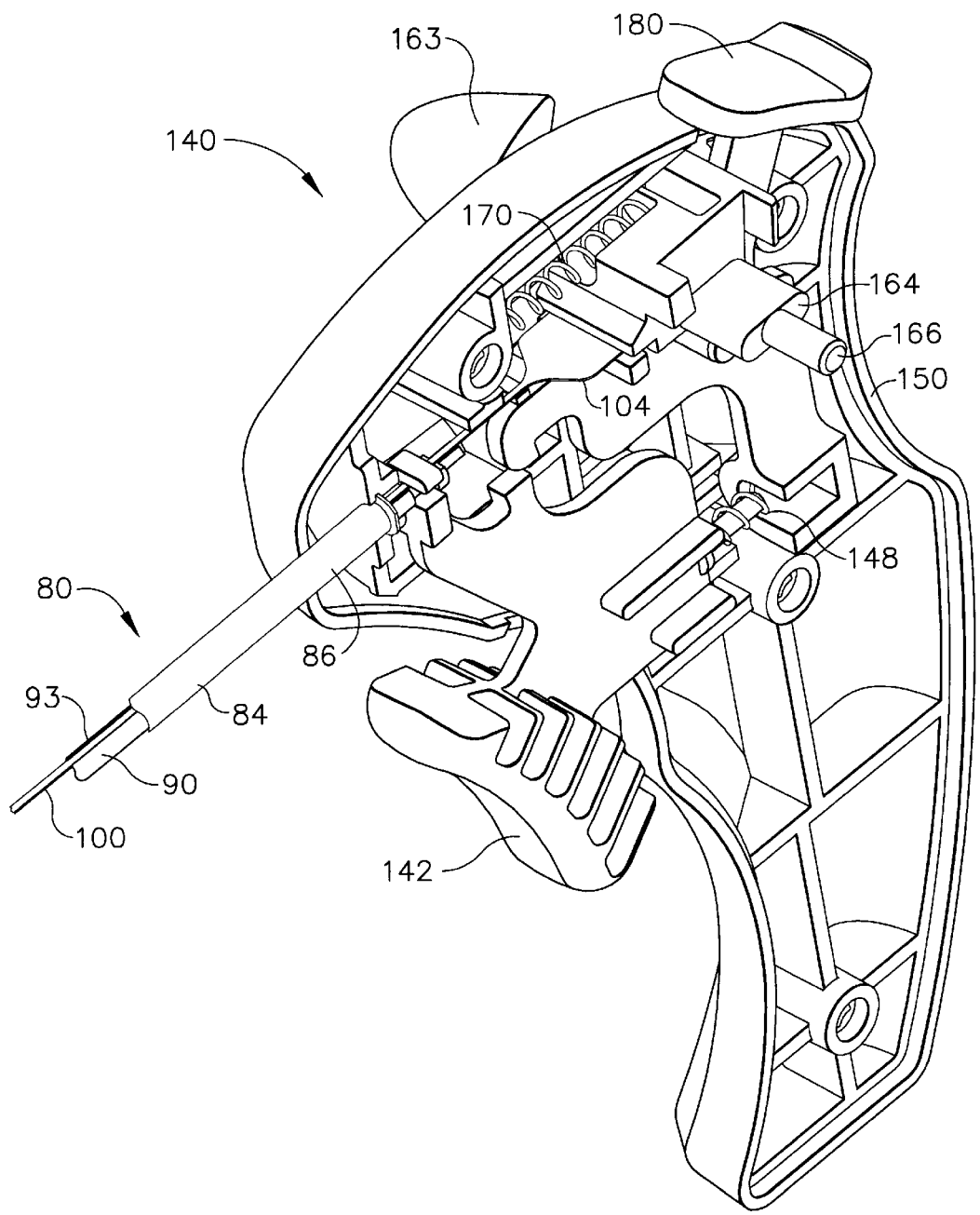
FIG. 5 is an isometric view of the handle and proximal portion of the shaft of the surgical device with the left side handle cover removed to reveal internal components.

FIG. 5 is an isometric view of the handle 140 without the left cover 152 and left button 162, and of the proximal portion of the shaft 80. The relative, assembled positions of the closing trigger 142, the slide 164, the release button 180 and the springs, 170 and 148, are shown in the ready-to-use or first position. Proximal end 104 of the drive member 100 is shown attached to slide 164 and positioned in track 93 of the closing member 90.

Figure 6:
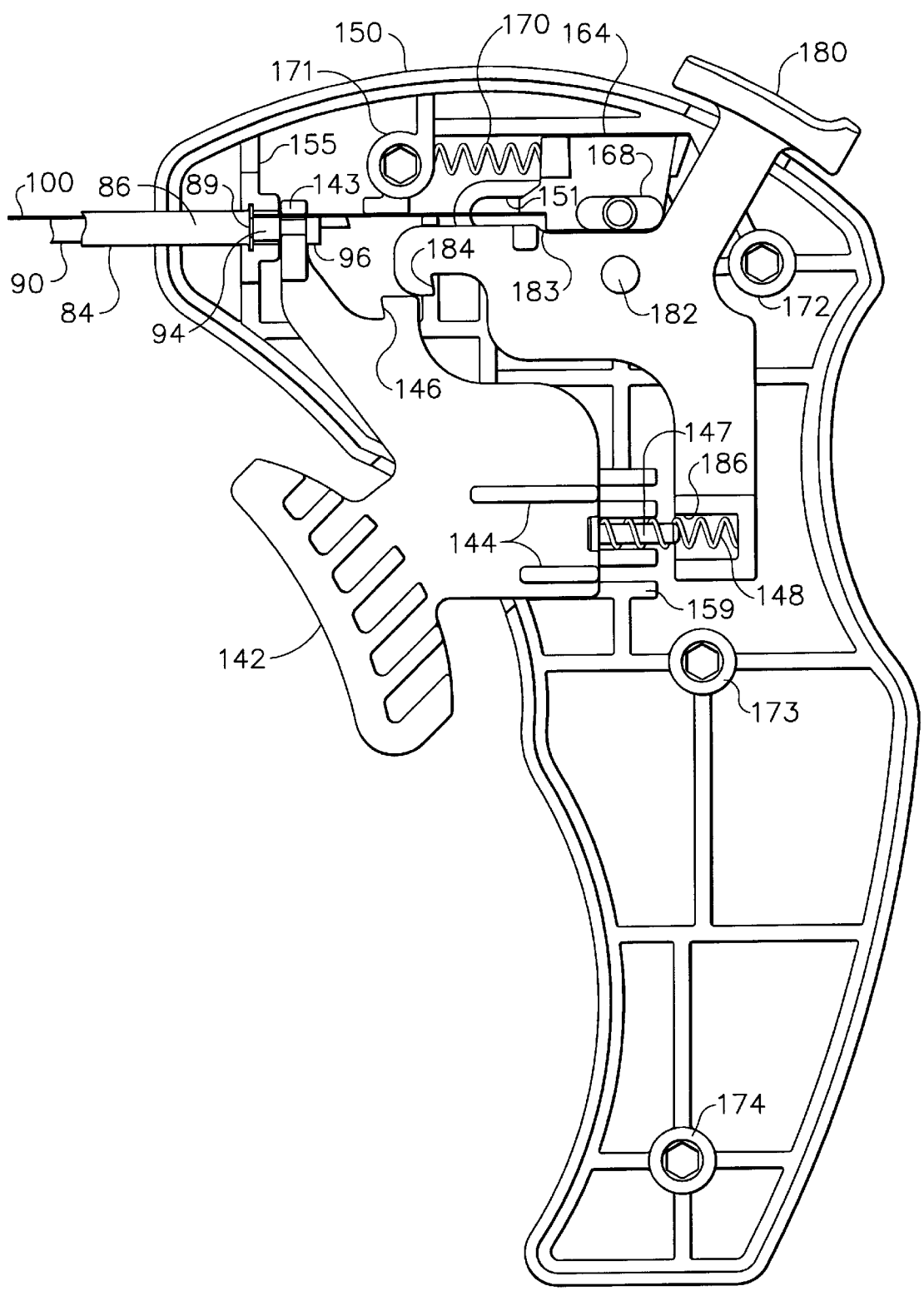
FIG. 6 is a side elevational view of FIG. 5 showing the instrument in a first position.

FIG. 6 is a side elevation of the same components and configuration, the first position, as shown in FIG. 5. All of the features of the right cover 150 are mirrored on the left cover 152 which is not shown. The closing trigger 142 is guided by fins 144 by right trigger ribs 159 of the right cover 150. The trigger spring 148 is captured on trigger spring post 147 of the closing trigger 142 and bears against cup end 186 of the release button 180. Trigger spring 148 therefore serves a double function as a return spring for the closure trigger 142 as well as for the release button 180. A rod flange 96 on the distal end 94 of closing member 90 is shown mounted into the rod retaining end 143 of closing trigger 142. Tube flange 89 on distal end 86 of tube 84 is shown mounted in tube retaining rib 155 of right cover 150. The slide 164 is in the extreme right position and is constrained by right slide tab 169 (see FIG. 3) slidably inserted in right slot 151 to move in the left, horizontal direction. Spring 170 pushes off first attachment boss 171 and justifies slide 164 to the extreme right position. The left, horizontal movement of slide 164 is blocked by step 183 of the release button 180. Trigger hook 146 of closing trigger 142 and release button hook 184 of release button 180 are not engaged. Attachment bosses 171, 172, 173, and 174 press fit with matching gripper pins on the inside wall of the left side cover 152.

Figure 7:
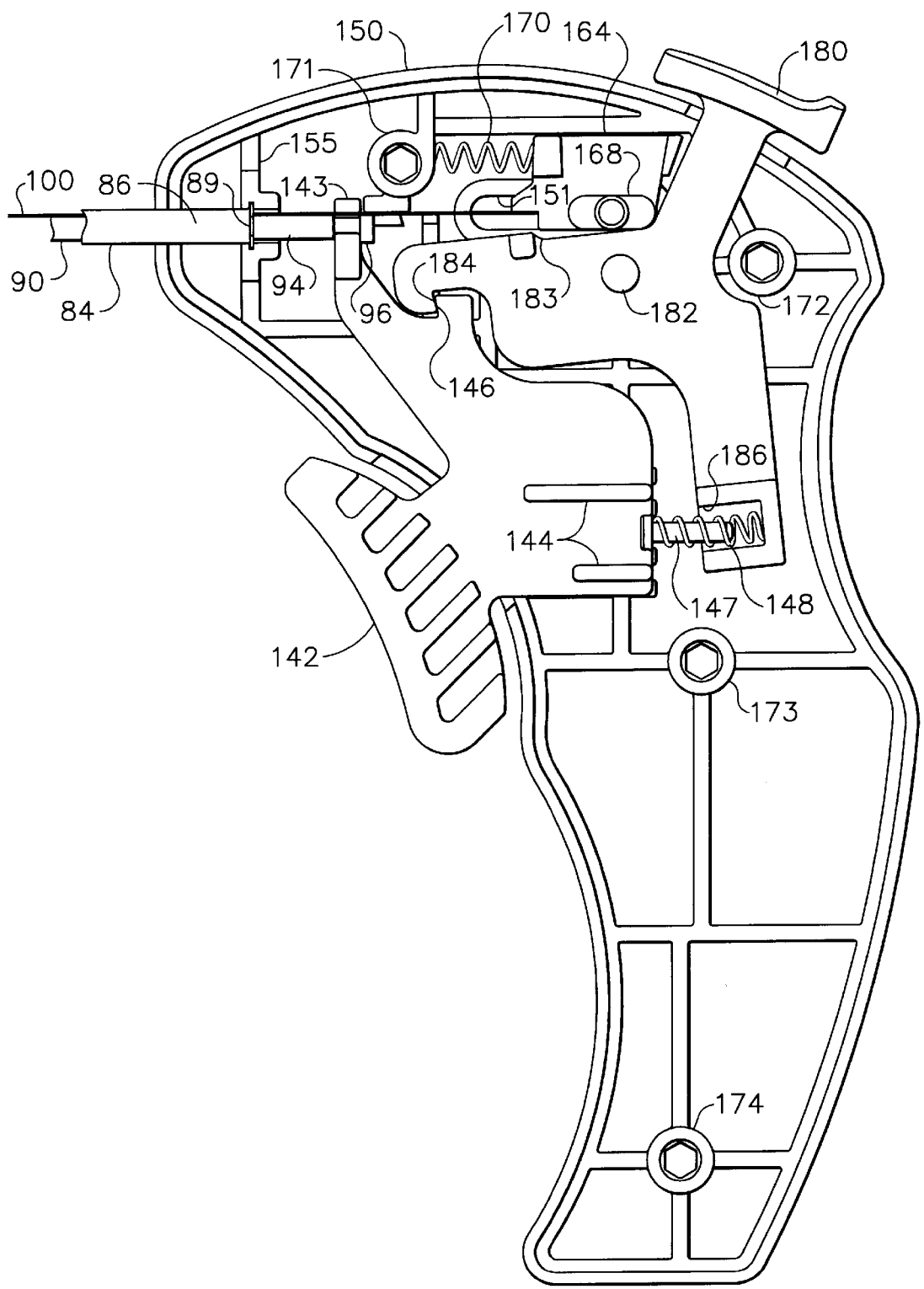
FIG. 7 is a side elevational view of FIG. 5 showing the instrument in an second position in which the closing trigger has been pulled.

FIG. 7 is the same, side elevational view of the components shown in FIG. 6, but with the closing trigger 142 and the release button 180 now moved to a second position. The actuator 164 is still in the extreme right position, but is no longer blocked by step 183 of release button 180. The closure trigger 142 has been pulled by the user to the second position and is held there by engagement of the trigger hook 146 with the release button hook 184 which has swung to the second position by the pivoting of the release button 180 about a release button pivot 182. Rod flange 96 of closure rod 90 has moved longitudinally to the second position within the stationary, tube 84. Drive member 100 is still shown in its first position. Actuation of the actuator 164 by the user causes the movement of the slide 164 in the left, horizontal direction, in turn causing the drive member 100 to move also in the left, horizontal direction. This movement causes the actuation of the work portion of the implement 20 as will be described.

FIGS. 8, 9, 10, 11, and 12 are side views in section of the implement 20 and distal end 82 of the shaft 80. These figures depict how the implement 20 clamps, staples, and transects bodily tissues. Referring first to FIG. 8, the implement 20 is shown in an open position, corresponding to the first position of the closing trigger 142 in FIG. 6. Channel 40, containing cartridge 60, is attached at its proximal end 44 to distal end 92 of closing member 90, with distal end 82 of tube 84 covering this attachment. Left finger 52 and right finger 53 on proximal end 44 of channel 40 (see FIG. 4) attach into distal end 92 of closing member 90. Pulling tab 38 of anvil 22 is captured inside of tube hole 83 on distal end 82 of tube 84. Tube surface 79 on distal end 82 of tube 84 rests in contact with anvil pushing surface 88 of anvil 22, while left and right guide posts, 28 and 29, of anvil 22 (see FIG. 4) are positioned inside of left and right anvil slots, 46 and 47 (see FIG. 8), of channel 40, thus determining the maximum angle 76 to which the anvil 22 can open to. A flexible rod portion 91 of closure member 90 is shown contained within bend 81 of tube 84. Distal end 102 of drive member 100 is positioned longitudinally approximately even with the surface 79 on distal end 82 of tube 84. Wedge 138, drivers 120, and knife 110 are shown retracted within the cartridge 60 in a first position.

Going next to FIG. 9, the implement 20 is shown in the closed position, creating a tissue gap 58 which is appreciably smaller than twice the typical wall thickness of blood vessels. An elongated region 12 is determined by the longitudinal span of the drivers 120 and is approximately equal to the length of each row of staples. The distal end 92 of closing member 90 has retracted to the second position by actuation of the closing trigger 142 (see FIG. 7) as described earlier. Flexible portion 91 of closing member 90 has conformed to bend 81 of tube 84. The channel 40 has been pulled further into distal end 82 of tube 84 while tube surface 79 has pushed against anvil surface 88 to cause the simultaneous rotation and sliding of guide posts 28 and 29 of anvil 22 (see FIG. 4) inside of the anvil slots 46 and 47 (FIG. 4) of the channel 40. Distal end 102 of drive member 100 has not moved, but the retraction of channel 40 into tube 84 has caused wedge 138 to move in close proximity to distal end 102. Cutting edge 112 of knife 110 is aligned with knife slot 26 of anvil 22, as are staples 130 with their respective staple pockets 24 (see FIG. 4) of anvil 22. This configuration corresponds to FIG. 7.

Figure 10:
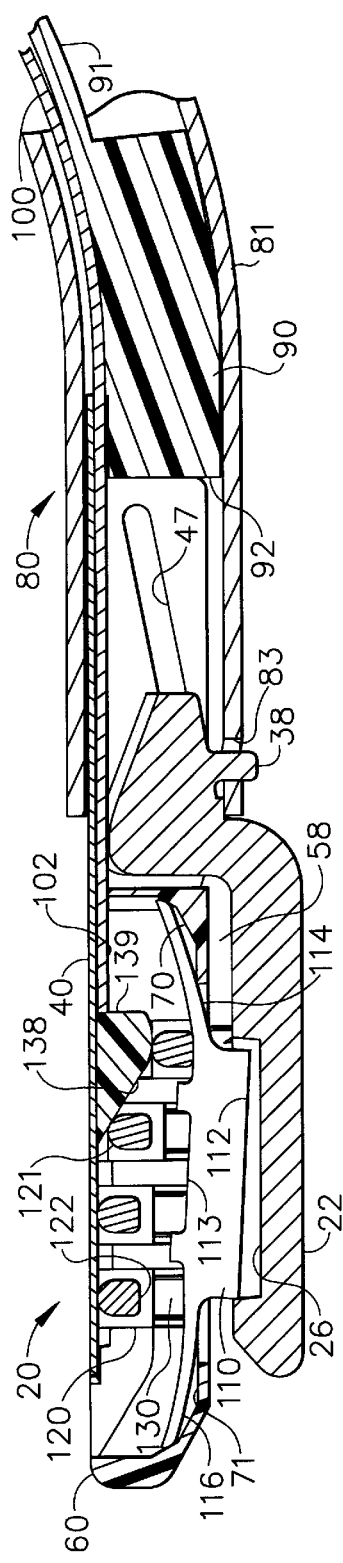
FIGS. 10, 11, and 12 are proceeding sequential positions of the components of the implement during instrument actuation.

In FIG. 10, the actuation of the work portion of the cartridge 60 has begun. Distal end 102 of drive member 100 is shown pushing against blunt edge 139 of wedge 138, due to the user pushing on the actuator 160 (see FIG. 1) on the handle 140. As wedge 138 moves horizontally in the right to left (distal) direction, it imparts a vertical force onto driver cam surface 121, causing driver 120 to move downward towards anvil 22. Driver bottom surface 122 pushes down on knife blunt edge 113 to cause a portion of knife cutting edge 112 to project into tissue gap 58, thus cutting any tissues contained within. The first and second ends 114 and 116 of the knife 110 are captured by proximal and distal ledges 70 and 71 of cartridge 60, and are shown deflecting. Simultaneously the driver 120 pushes down on a pair of staples 130, forcing them out of cartridge 60 and towards anvil 22. The staples 130 are formed in the staple pockets 24 into B-shapes or other variations, thus fastening together the tissues contained in the tissue gap 58.

Figure 11:
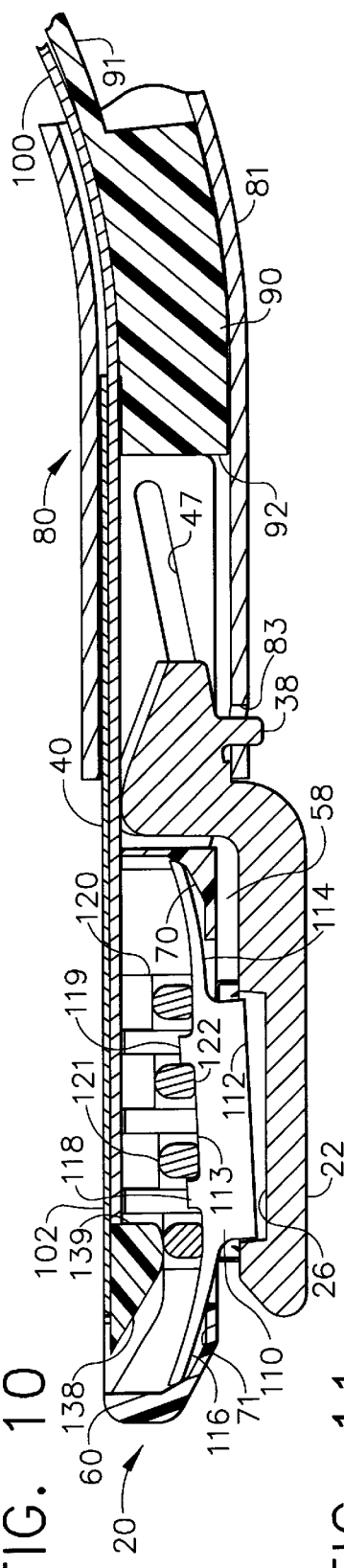

FIG. 11 depicts the formation of the most distal pair of staples 130 and the completion of the tissue transection by the knife 110. First knife tab 118 and second knife tab 119 serve to keep the knife positioned in longitudinal alignment with the knife slot 26 of the anvil 22. The knife tabs 118 and 119 locate on the driver bottom surfaces 122 of the middle two driver pairs.

Figure 12:
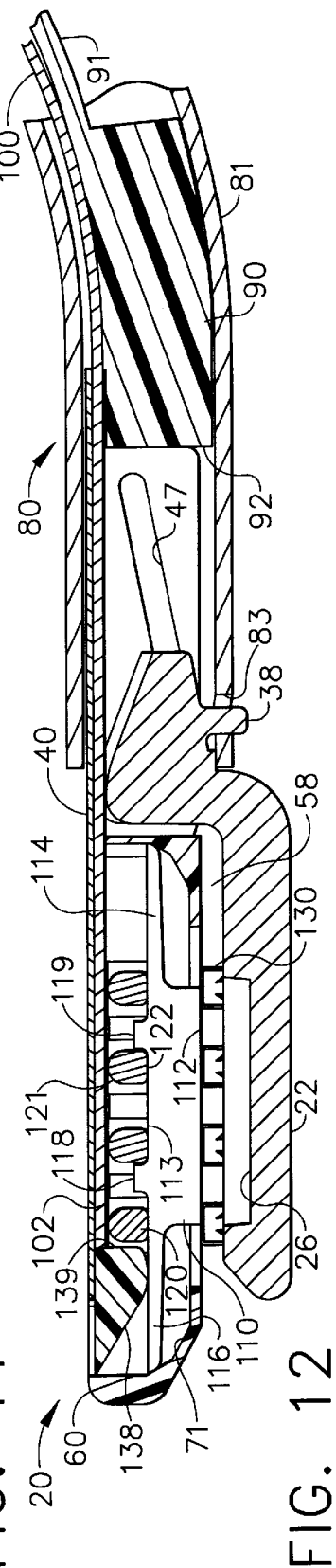

FIG. 12 shows the completion of the work portion actuation sequence. The wedge 138 has reached the distal most position within the cartridge 60 as the drive member 100 has completed its movement to the left. Knife ends 114 and 116 of knife 110 have sprung back to their original shapes, thus lifting the knife 110 back inside of the cartridge 60 to protect the cutting edge 112. The eight staples 130 are fully formed and aligned into two rows extending slightly beyond each end of the cut made in the tissues. The wedge 138 is locked into the distal end 68 of the cartridge 60 by the distal most driver 120. All of the drivers 120 are held in their first, preferred positions by knife 110. When the user releases the actuator 160 (see FIG. 7), it returns to its first position and enables the release button 180 to be pushed. The user may next release the implement 20 from the tissue by pressing the release button 180 (see FIG. 7) which allows the closing member 90 to move distally and to push the channel 40 out of the distal end 82 of tube 84. As this occurs, pulling tab 38 of anvil 22 is held from moving horizontally by tube hole 83 of tube 84. The anvil slots, 46 and 47, slide over the anvil guide posts 28 and 29, as before but in the reverse direction, and the anvil 22 pivots to the open position as shown in FIG. 8, thus releasing the tissues contained within the tissue gap 58.

Figure 13:
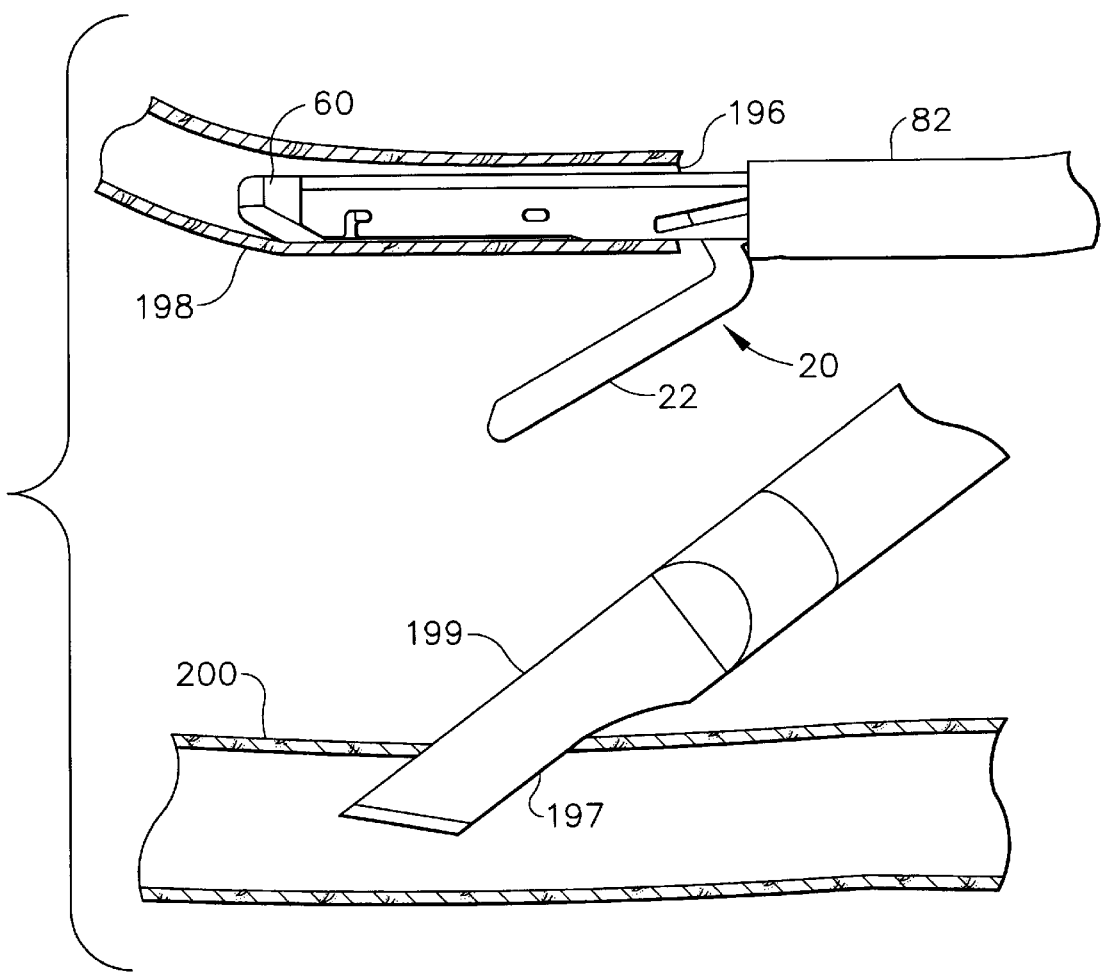
FIG. 13 is a side elevational view of the implement located in the prepared graft vessel. The target vessel is also shown and is being prepared by manual incising.
Figure 14:
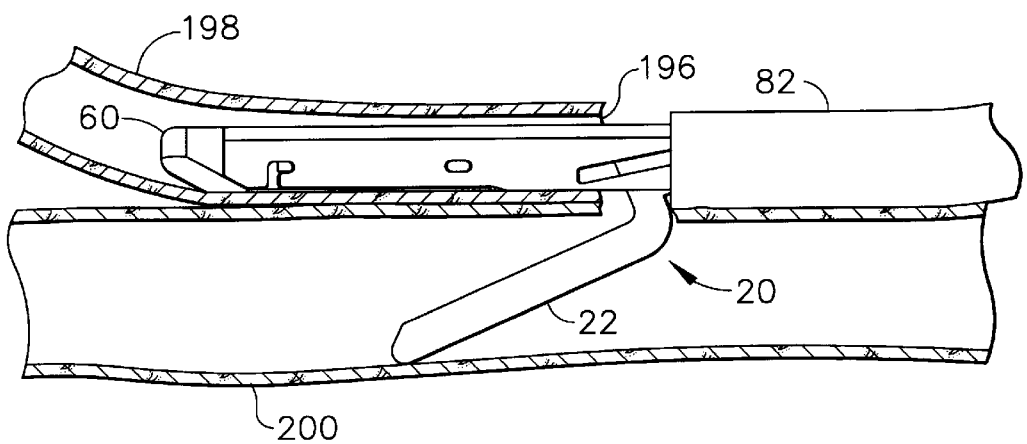
FIG. 14 is a side elevational view of the implement correctly located, achieving proximity of the graft and target vessels.
Figure 15:
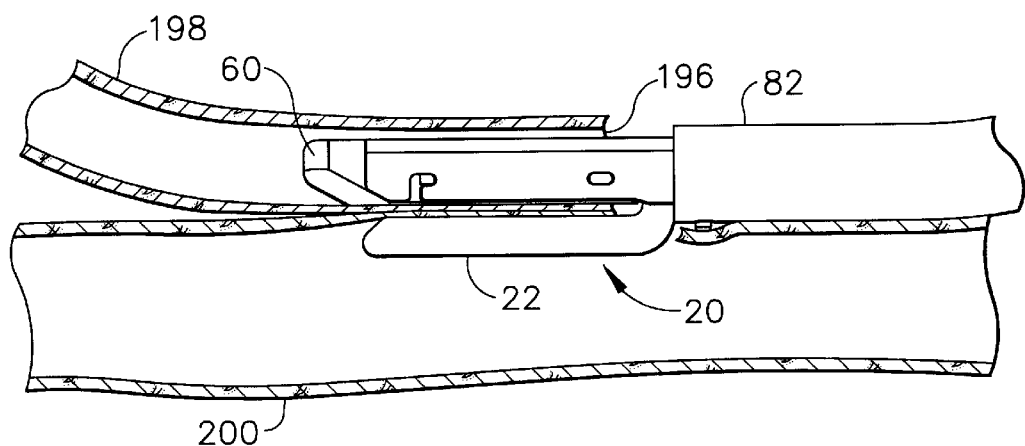
FIG. 15 is a side elevational view of the implement with the anvil in an actuated position thus holding the vessels together for simultaneous cutting and stapling.
Figure 16:
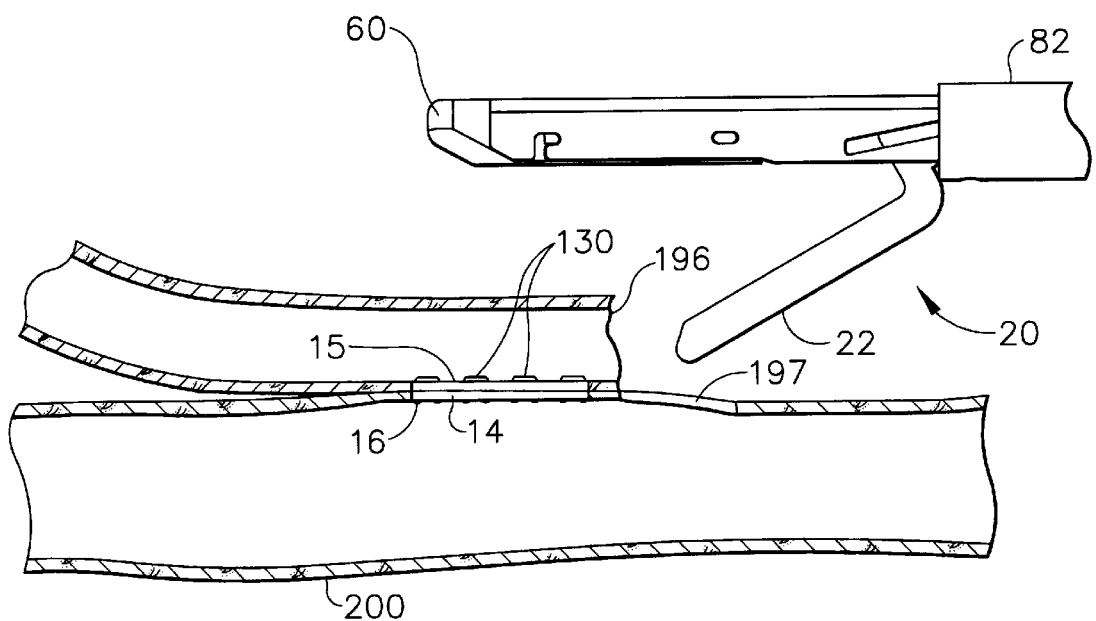
FIG. 16 is a side elevational view of the implement removed from the vessels.

FIGS. 13, 14, 15, and 16 show the distal portion of the present invention as it is being used to anastomose a graft blood vessel 198 to a target blood vessel 200. After the graft vessel 198 and target vessel 200 have been prepared for the anastomosis by removing fat and muscle tissues from the areas to be joined, an incision 197 is made in the target vessel 200 by using a scalpel 199 or other cutting means. The length of incision 197 need be only long enough to allow the insertion of the anvil 22 of the implement 20. During the next steps, the surgeon holds the handle 140 of the surgical device 10 (see FIG. 1) and operates the closing trigger 142, the actuator 160, and the release button 180 with the same hand, thus using the free hand to position the blood vessels. FIG. 13 depicts how the cartridge 60 is inserted into an open end 196 of a graft blood vessel 198 as far as possible without putting folds into the vessel. Next the anvil 22 is inserted into the incision 197 of the target vessel 200, as shown in FIG. 14. FIG. 15 shows the implement 20 clamped onto the graft and target vessels, 198 and 200, compressing the two adjoining walls of the vessels in the region to be stapled and transected. The actuator 160 (see FIG. 1) is pushed completely to the end of its stroke within the handle 140 so that the graft vessel 198 is stapled to target vessel 200 and a communicating passageway is cut between the joined vessels by the knife 110, as shown in the sequences in FIGS. 10, 11, and 12. The release button 180 (see FIG. 1) is next pushed to allow the anvil 22 to open away from the cartridge 60, and the implement 20 is removed from the graft and target vessels, 198 and 200, as shown in FIG. 16. The surgical device 10 may then be discarded. The open end 196 and the incision 197 are next closed using clips, hand suturing, or any other techniques known to those skilled in the art, to complete the anastomosis. A passageway 14 is shown between blood vessels 198 and 200 with the eight surgical wire staples 130 holding together the graft vessel incision peripheral edge 15 to the target vessel incision peripheral edge 16. The incision peripheral edges, 15 and 16, were created together by the same cutting action and therefore are exactly the same length and are exactly aligned and held adjacent to each other so that the healing together of the blood vessels by the formation of a smooth endothelial lining is promoted. What is more, the passageway 14 has no interruptions in its perimeter, and is still flexible to accommodate the pulsing blood flow within.

While a preferred embodiment of the present invention has been shown and described herein, it will be obvious to those skilled in the art that such an embodiment is provided by way of example only. Numerous variations, changes, and substitutions will now occur to those skilled in the art without departing from the invention. Accordingly, it is intended that the invention be limited only by the spirit and scope of the appended claims.

What is claimed is:

1. A surgical device for joining a first and a second vessel together, said device comprising:

a) an implement having proximal and distal ends and a longitudinal axis extending therebetween, said implement having a bottom member and a top member which are substantially coextensive and are pivoted together at said proximal end so that a wall of each of said first and second vessels can be held between said top and bottom portions;

b) a means for joining said first and second vessels together along two joining lines substantially parallel to each other and to said longitudinal axis of said implement, said lines having distal and proximal ends; and c) a knife having a longitudinal cutting edge for severing said first and second vessels between said joining lines so as to create a passageway through said vessels, said means for severing said vessels is able to cut said vessels along a cut line having a proximal end distal to said proximal ends of said joining lines, and a distal end proximal to said distal ends of said joining lines.

2. The device according to claim 1 wherein said a means for joining said first and second vessels along two joining lines comprises a means for applying a plurality of staples so as to join said vessels along said joining lines.

3. The device according to claim 2 wherein said means for applying said plurality of staples along said joining lines moves longitudinally such that said staples are first applied at the proximal ends of said join lines and continue to the distal end of said joining lines.

4. The device according to claim 3 wherein said means for severing said first and second vessels operates longitudinally such that said vessels are first severed at the proximal end of said cut line and continues to the distal end of said cut lines.

5. The device according to claim 4 wherein said means for severing said first and second vessels severs said vessels along said cut line after said staples have been applied to corresponding locations along said joining lines.

* * * * *